United States Patent [19]
Taniguchi et al.

[11] Patent Number: 5,153,217
[45] Date of Patent: Oct. 6, 1992

[54] PYRROLEALDEHYDE DERIVATIVE

[75] Inventors: Masao Taniguchi; Tadashi Shirasaka, both of Machida; Kohei Umezu, Yokohama; Mayumi Hirata, Machida, all of Japan

[73] Assignee: Mitsubishi Kasei Corporation, Tokyo, Japan

[21] Appl. No.: 630,044

[22] Filed: Dec. 19, 1990

[30] Foreign Application Priority Data

Dec. 20, 1989 [JP] Japan .................. 1-330256

[51] Int. Cl.⁵ .............. A61K 31/40; C07D 207/333
[52] U.S. Cl. ................................. 514/423; 548/530
[58] Field of Search .................... 548/530; 514/423

[56] References Cited

U.S. PATENT DOCUMENTS

| | | |
|---|---|---|
| 2,479,971 | 8/1949 | Scholz . |
| 2,479,972 | 8/1949 | Scholz . |
| 2,500,713 | 3/1950 | Sickels et al. . |
| 4,382,143 | 5/1983 | Shepherd . |
| 4,560,700 | 12/1985 | Schnettler et al. . |
| 4,824,958 | 4/1989 | Cetenko et al. . |

OTHER PUBLICATIONS

Muchowski et al., Tet. Lett., vol. 29, No. 26, pp. 3215–3218, 1988.
Muchowski et al., Helv. Chim. Acta 67(4) 1168–1172 (1984).
J. Org. Chem. 1980, 45, pp. 4980–4982, "Metabolites of the Marine Sponge Laxosuberites sp".
J. Org. Chem, vol. 37, No. 7, 1972, pp. 925–929.
Journal of the American Chemical Society, vol. 91, No. 14, 1969, pp. 3931–3938.
Journal of Organic Chemistry, vol. 37, No. 23, 1972, pp. 3618–3622.
Synthesis, No. 4, 1989, pp. 337–340.

*Primary Examiner*—Nicky Chan
*Attorney, Agent, or Firm*—Oblon, Spivak, McClelland, Maier & Neustadt

[57] ABSTRACT

A novel pyrrolealdehyde derivative represented by the following formula (I):

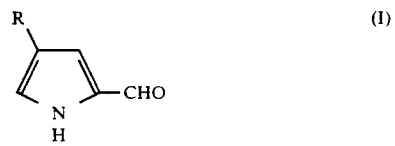

wherein R represents $C_{10}$–$C_{16}$ alkyl unsubstituted or substituted by at least one substituent selected from the group consisting of halo, hydroxy, amino, carbamoyl, $C_1$–$C_5$ alkylamino, $C_2$–$C_6$ dialkylamino, $C_2$–$C_6$ acylamino, $C_1$–$C_5$ alkylthio, mercapto, $C_2$–$C_6$ acyloxy, carbamoyloxy, $C_6$–$C_{12}$ aryl and $C_3$–$C_7$ cycloalkyl; or $C_{10}$–$C_{16}$ alkenyl having at least one vinyl, and a pharmaceutically acceptable salt thereof are provided. The compounds are highly effective in reducing the level of triglyceride and cholesterol in serum, and useful as an active ingredient of a pharmaceutical composition for treating hyperlipemia and arteriosclerosis.

3 Claims, No Drawings

PYRROLEALDEHYDE DERIVATIVE

BACKGROUND OF THE INVENTION

The present invention relates to a pyrrolealdehyde derivative which has an excellent activity of reducing lipids and, therefore, useful as a therapeutical medicine for hyperlipemia.

Heretofore, it has been considered that a metabolic disorder of lipids such as triglyceride and cholesterol in blood is one of the major dangerous factors causing an normal increase in or imbalance of a level of lipids in blood, which results in arteriosclerosis as well as ischemic heart disease such as angina pectoris and myocardinal infarction, and cerebral infarction.

As a medicine for hyperlipemia, clofibrate type medicine, nicotinic acid and derivative thereof have been mainly used so far. Although they reduce the level of triglyceride in blood, they are less effective in reducing the cholesterol. Further, probucol having a new structure or cholestyramine which is an anion exchange resin, has been used in recent years as the medicine for reducing the blood level of cholesterol, but they are contrarily inactive to the triglyceride.

The abnormal increase in the blood level of either triglyceride or cholesterol is a major factor for the arteriosclerosis, in particular, atherosclerosis. It has especially been known that the risk of the onset of those diseases is remarkably increased if both types of lipids are increased simultaneously.

As described in the foregoing, although the medicines for reducing the level of triglyceride or cholesterol in blood have already been used clinically, it is further demanded to develop a more potent medicine which has little adverse reaction and is preferable also in the dosage, safety and application. In particular, much attention has been focused to the development of a medicine capable of effectively reducing both of the levels of triglyceride and cholesterol in blood together in view of the therapy and prevention of diseases caused by arteriosclerosis such as ischemic heart disease and cerebral infarction, but such medicine capable of satisfying these requirements has yet been found.

SUMMARY OF THE INVENTION

It has been found by the present inventors that a specific class of pyrrolealdehyde derivative is effective in reducing both of the levels of triglyceride and cholesterol in blood as compared with the conventional medicines. The present invention has been accomplished based on this finding.

The present invention provides a pyrrolealdehyde derivative represented by the following formula (I):

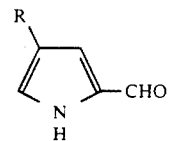

(I)

wherein R represents unsubstituted or substituted alkyl or an alkenyl, and a pharmaceutically acceptable salt thereof.

DETAILED DESCRIPTION OF THE INVENTION

The alkyl represented by R in the formula (I) may include a $C_{10}$-$C_{16}$ alkyl such as decyl, undecyl, 2,2-dimethylundecyl, 11,11-dimethyldodecyl, dodecyl, 12-methyltridecyl, tridecyl, 12,12dimethyltridecyl, tetradecyl, 6,6-dimethyltetradecyl, pentadecyl and hexadecyl. As example of the substituent for the alkyl, halo atom such as fluorine, chlorine, bromine and iodine; hydroxyl; amino; carbamoyl; $C_1$-$C_5$ alkylamino such as methylamino, ethylamino, n-propylamino, i-propylamino, n-butylamino, t-butylamino and n-pentylamino; $C_2$-$C_6$ dialkylamino such as dimethylamino, methylethylamino, diethylamino and dipropylamino; $C_2$-$C_6$ acylamino such as acetylamino, propionylamino, butyrylamino, isobutyrylamino, valerylamino, pivaloylamino and hexanoylamino; $C_1$-$C_5$ alkylthio such as methylthio, ethylthio, n-propylthio, i-propylthio, n-butylthio, t-butylthio and n-pentylthio; mercapto; $C_2$-$C_6$ acyloxy such as acetoxy, propionyloxy, butyryloxy, isobutyryloxy, valeryloxy, pivaloyloxy and hexanoyloxy; carbamoyloxy; $C_6$-$C_{12}$ aryl such as phenyl, tolyl, xylyl and naphthyl; and $C_3$-$C_7$ cycloalkyl such as cyclopropyl, cyclobutyl, cyclopentyl, cyclohexyl and cycloheptyl. In the present invention, a pyrrolealdehyde derivative in which the unsubstituted or substituted alkyl has 12 to 14 carbon atoms is preferred.

As example of the alkenyl represented by R, $C_{10}$-$C_{16}$ alkenyl, preferably $C_{12}$-$C_{14}$ alkenyl, having at least one vinyl group, such as 1-decenyl, 4,7-decadienyl, 10-methyl-9-undecenyl, 2-undecenyl, 4,8-dimethyl-3,7-nonadienyl, 1-dodecenyl, 2-tridecenyl, 6-tridecenyl, 1-tetradecenyl, 3,7,11-trimethyl-2,6,10-dodecatrienyl, 1-pentadecenyl and 1-hexadecenyl.

The pharmaceutically acceptable salts of the pyrrolealdehyde derivative may include a salt formed from the pyrrolealdehyde derivative of the formula (I) and an inorganic acid such as hydrochloric acid, hydrobromic acid and sulfuric acid or an organic acid such as maleic acid, succinic acid and citric acid.

Examples of the pyrrolealdehyde derivative of the present invention are listed in the following Table 1.

TABLE 1

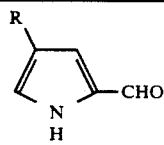

| Compound No. | R |
| --- | --- |
| 1 | $CH_3(CH_2)_9-$ |
| 2 | $CH_3(CH_2)_{10}-$ |
| 3 | $CH_3(CH_2)_{11}-$ |
| 4 | $CH_3(CH_2)_{12}-$ |
| 5 | $CH_3(CH_2)_{13}-$ |
| 6 | $CH_3(CH_2)_{14}-$ |

TABLE 1-continued

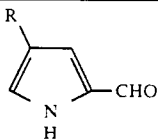

| Compound No. | R |
|---|---|
| 7 | $CH_3(CH_2)_{15}-$ |
| 8 | $(CH_3)_3C(CH_2)_8-$ |
| 9 | $(CH_3)_3C(CH_2)_{10}-$ |
| 10 | $(CH_3)_2CH(CH_2)_{10}-$ |
| 11 | $(CH_3)_3C(CH_2)_{11}-$ |
| 12 | $CH_3(CH_2)_5C(CH_3)_2(CH_2)_5-$ |
| 13 | $CH_3(CH_2)_8C(CH_3)_2CH_2-$ |
| 14 | cyclohexyl-$(CH_2)_8-$ |
| 15 | cyclopentyl-$(CH_2)_8-$ |
| 16 | $(CH_3)_2CH(CH_2)_3CH(CH_3)(CH_2)_3-$ |
| 17 | phenyl-$(CH_2)_8-$ |
| 18 | $Cl(CH_2)_{12}-$ |
| 19 | $CH_3(CH_2)_{11}CHBr-$ |
| 20 | $HO(CH_2)_{12}-$ |
| 21 | $CH_3(CH_2)_5CH(OH)(CH_2)_5-$ |
| 22 | $H_2N(CH_2)_{12}-$ |
| 23 | $H_2NOC(CH_2)_{12}-$ |
| 24 | $C_2H_5NH(CH_2)_{12}-$ |
| 25 | $(CH_3)_2N(CH_2)_{12}-$ |
| 26 | $CH_3(CH_2)_2CONH(CH_2)_{11}-$ |
| 27 | $CH_3(CH_2)_{11}CH(SCH_3)-$ |
| 28 | $CH_3(CH_2)_{11}CHSH-$ |
| 29 | $CH_3COO(CH_2)_{12}-$ |
| 30 | $CH_3(CH_2)_5CH(OCOCH_3)(CH_2)_5-$ |
| 31 | $H_2NOCO(CH_2)_{12}-$ |
| 32 | $CH_3(CH_2)_{10}CH=CH-$ |
| 33 | $CH_3(CH_2)_9CH=CHCH_2-$ |
| 34 | $(CH_3)_2C=CH(CH_2)_2C(CH_3)=CH-CH_2-$ |
| 35 | $CH_3(CH_2)_5CH=CH(CH_2)_5-$ |
| 36 | $(CH_3)_2C=CH(CH_2)_8-$ |
| 37 | $CH_3(CH_2)_{11}CH=CH-$ |
| 38 | $CH_3(CH_2CH=CH)_2(CH_2)_3-$ |
| 39 | $(CH_3)_2C=CH(CH_2)_2C(CH_3)=CH(CH_2)_2-$ |
| 40 | $(CH_3)_2C=CH(CH_2)_2C(CH_3)=CH(CH_2)_2C(CH_3)=CHCH_2-$ |

The pyrrolealdehyde derivative of the present invention can be produced, for example, by the following methods.

Method 1:

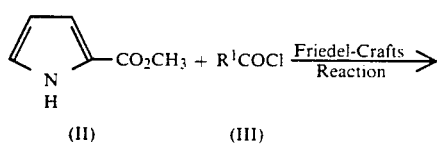

Method 1:

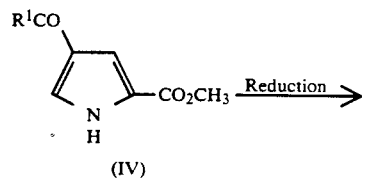

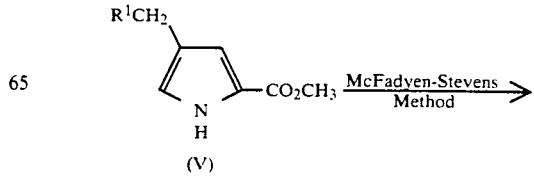

Method 1:

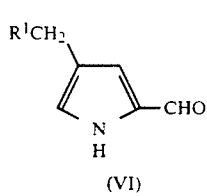

In the above formulae, R¹CH₂— represents alkyl and alkenyl.

Methyl pyrrole-2-carboxylate (II) and an appropriate acylchloride (III) are subjected to Friedel-Crafts reaction in the presence of a Lewis acid such as aluminum chloride, stannic chloride and boron trifluoride diethyl etherate in a solvent such as benzene, methylene chloride and carbon disulfide at a temperature of $-10°$ C. to the boiling point of the solvent used to obtain methyl 4-acylpyrrole-2-carboxylate (IV). The thus obtained methyl 4-acylpyrrole-2-carboxylate (IV) can be converted to methyl 4-alkyl(or 4-alkenyl)pyrrole-2-carboxylate (V) by reducing the carbonyl group by means of an appropriate reduction reaction such as diborane reduction, Raney nickel reduction of dithioketal and contact hydrogenation of an acetate formed through an alcohol. The compound (V) can be converted to a compound (VI) of the present invention through three steps by McFadyen-Stevens method described in Organic Reactions, 8, 232 (1954).

Method 2:

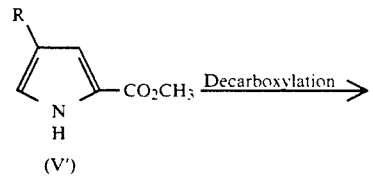

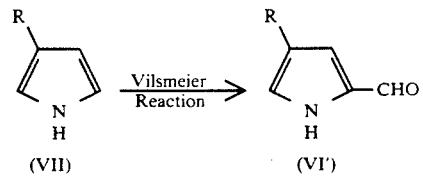

In the above formulae, R— is the same as defined above.

When methyl 4-alkyl(or 4-alkenyl)pyrrole-2-carboxylate (V') is heated at a higher temperature (100° to 200° C.) in an alcoholic solvent such as ethylene glycol and diethylene glycol containing water in the presence of a base such as sodium hydroxide and potassium hydroxide, hydrolysis of the ester group and decarboxylation take place simultaneously, thereby yielding 3-alkyl(or 3-alkenyl)pyrrole (VII) almost quantitatively. A compound (VI') of the present invention can be obtained by subjecting the compound (VII) to Vilsmeier reaction using a combination of dimethylformamide and phosphorus oxychloride or N-methylformanilide and phosphorus oxychloride.

Method 3:

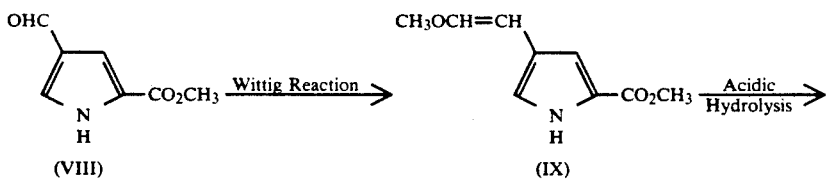

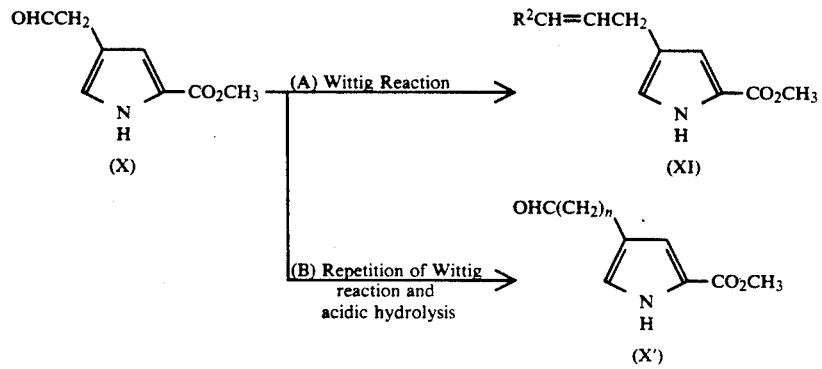

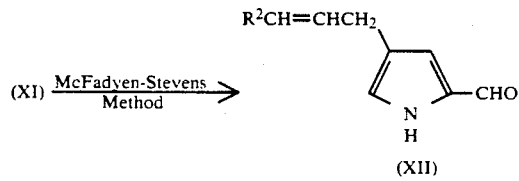

Method 3:

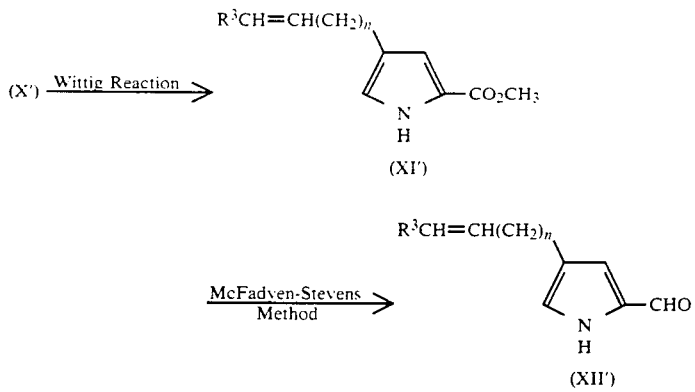

In the above formulae, $R^2CH=CHCH_2—$ and $R^3CH=CH(CH_2)_n—$ are the same alkenyl as defined for R in the formula (I), n is a number of repetition of the reaction (B) and integer of not less than 2.

The compound (IX) is obtained by subjecting methyl 4-formylpyrrole-2-carboxylate (VIII) (Bulletin de la Societe Chemique de France, 283 (1972)) to Wittig reaction with methoxymethyltriphenylphosphonium chloride in the presence of a base such as lithium diisopropyl amide and butyl lithium. The compound (IX) is then subjected to hydrolysis in an alcoholic solvent containing water in the presence of an acidic catalyst such as sulfuric acid and p-toluenesulfonic acid to give (2-methoxycarbonylpyrrole)-4-acetaldehyde (X). In reaction path (A), cis- and/or trans methyl 4-alkenyl-pyrrole-2-carboxylate (XI) is obtained by further reacting the compound (X) with alkyltriphenylphosphonium bromide under the condition of Wittig reaction. The compound (XI) can be converted to a compound (XII) of the present invention by McFadyen-Stevens reaction in the same manner as in Method 1. In reaction path (B), the compound (X) is converted to a compound (X') by repeating desired times Wittig reaction and acidic hydrolysis in the same manner as in the reactions of (VIII)→(IX) and (IX)→(X). A compound (XII') of the present invention having a double bond in a desired position in the substituent is obtained by subjecting the compound (X') to the same reaction as in the reaction path (A).

Method 4:

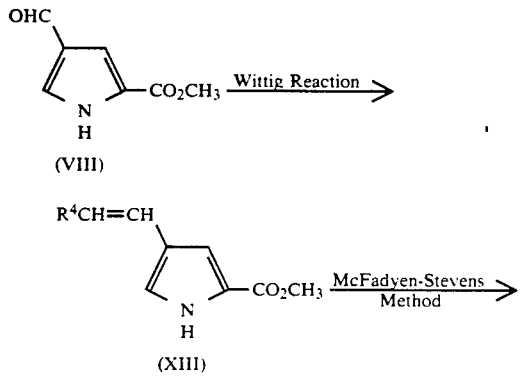

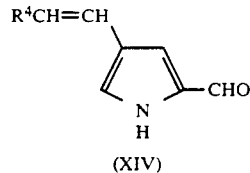

In the above formulae, $R^4CH=CH—$ is the same alkenyl as defined for R in the formula (I).

Cis- and/or trans methyl 4-alkenylpyrrole-2-carboxylate represented by formula (XIII) is obtained by reacting methyl 4-formylpyrrole-2-carboxylate with alkyl(or alkenyl)triphenylphosphonium bromide under the same Wittig reaction conditions as in Method 3. The thus obtained compound (XIII) can be converted to a compound (XIV) of the present invention in the same manner as in Method 1.

The pyrrolealdehyde derivative of the present invention is useful as an active ingredient of a pharmaceutical composition for treating hyperlipemia. The pharmaceutical composition comprises a therapeutically effective amount of a pyrrolealdehyde derivative and a pharmaceutically acceptable adjuvant. The composition may be administrated, preferably, orally to a patient, and the formulation for the oral administration may be tablet, granule, powder, capsule, etc. These formulations are prepared from the pyrrolealdehyde derivative and an adjuvant known in the art. Example of the adjuvant may include an excipient such as glucose, lactose, corn starch and mannitol, a binder such as hydroxypropyl-cellulose (HPC) and carboxymethylcellulose (CMC), a disintegrator such as starch and powdery gelatin, a lubricant such as talc and magnesium stearate, etc.

The dose of the pyrrolealdehyde derivative of the present invention, in the case of oral administration, is from 10 mg to 10 g, preferably, from 100 mg to 5 g per day for an adult, which may be administrated all at once or divisionally for 2 to 3 times.

The present invention is further illustrated in detail with reference to the following examples. It should be understood that the present invention is not limited solely to these examples.

SYNTHESIS EXAMPLE 1

Synthesis of methyl 4-tridecanoylpyrrole-2-carboxylate

In 480 ml of methylene chloride, were dissolved 102.9 g (0.48 mol) of tridecanoic acid, to which 52.6 ml (0.72 mol) of thionyl chloride and 0.2 ml of N,N-dimethylformamide were added to obtain a solution. The solution was allowed to stand over night and was evaporated under a reduced pressure. The remaining oil was added to 400 ml of methylene chloride containing 106.6 g (0.8 mol) of anhydrous aluminum chloride, to which 200 ml of methylene chloride solution containing 50.05 g (0.4 mol) of methyl pyrrole-2-carboxylate was added dropwise in 40 minutes at a temperature of 3° to 9° C. After the addition, the temperature of the mixture was elevated slowly up to room temperature and the mixture was stirred for 2 hours. Then, the mixture was poured into 800 ml of ice-water, and 1000 ml of methylene chloride was added thereto to dissolve all the crystals precipitated, followed by liquid separation. The organic layer was washed with water three times, dried over anhydrous magnesium sulfate and condensed under a reduced pressure. The residue was recrystallized from 400 ml of ethyl acetate and 400 ml of hexane to obtain 107.2 g of methyl 4-tridecanoylpyrrole-2-carboxylate as white crystals. The yield was 83% and the melting point was 92° to 93° C.

IR (KBr) cm$^{-1}$: 3270, 2920, 2855, 1690, 1660, 1565, 1455, 1385, 1290, 1215.

NMR (CDCl$_3$) δ: 0.88 (t, 3H), 1.15, 1.38 (each m, 18H), 1.65, 1.75 (each m, 2H), 2.75 (t, 2H), 3.89 (s, 3H), 7.28, 7.30 (each m, 1H), 7.53, 7.55 (each m, 1H), 9.52 (broad s, 1H).

SYNTHESIS EXAMPLE 2

Synthesis of dithioethyleneketal of methyl 4-tridecanoylpyrrole-2-carboxylate

Into 140 ml of acetic acid, was dissolved 18.29 g (56.9 mmol) of methyl 4-tridecanoylpyrrole-2-carboxylate obtained in Synthesis Example 1. To the solution, were added 14.0 ml (167 mmol) of 1,2-ethanedithiol and 14 ml of boron trifluoride diethyl etherate, and stirred overnight under cooling with water. The solution was evaporated and 100 ml of water was added to the residue, followed by extraction with 200 ml (100 ml×2) of ethyl acetate. The combined extract was washed with a 5% aqueous solution of sodium hydroxide and then washed with a saturated aqueous solution of sodium chloride, followed by drying over anhydrous magnesium sulfate and evaporation. The residue was recrystallized from a mixed solvent of ethyl acetate and hexane to obtain dithioethyleneketal of methyl 4-tridecanoylpyrrole-2-carboxylate. The titled compound remained in the mother liquor was collected by silica-gel column chromatography (eluent: ethyl acetate/hexane=1/6). The total yield was 15.44 g (68%) and the melting point was 77° to 78° C.

IR (KBr) cm$^{-1}$: 3360, 2940, 2860, 1705, 1440, 1385, 1265, 1210, 1120.

NMR (CDCl$_3$) δ: 0.88 (t, 3H), 1.20, 1.40 (each m, 20H), 2.22, 2.28 (each m, 2H), 3.25, 3.41 (each m, 4H), 3.84 (s, 3H), 6.92 (s, 1H), 7.05, 7.07 (each m, 1H), 9.08 (broad s, 1H).

SYNTHESIS EXAMPLE 3

Synthesis of methyl 4-tridecylpyrrole-2-carboxylate

Into a mixture of 150 ml of Raney nickel (activated type, produced by Aldrich Co.), which had been washed with water and then ethanol, and 750 ml of ethanol, was added 15.06 g (37.9 mmol) of dithioethyleneketal of methyl 4-tridecanoylpyrrole-2-carboxylate obtained in Synthesis Example 2. The mixture was refluxed for 30 minutes and cooled to about 30° C. After removing Raney nickel, the mixture was evaporated. The residue was recrystallized from ethanol to obtain 10.70 g of methyl 4-tridecylpyrrole-2-carboxylate as white crystals. The yield was 91.8% and the melting point was 80° to 82° C.

IR (KBr) cm$^{-1}$: 3340, 2920, 2850, 1690, 1445, 1390, 1265, 1205, 1130.

NMR (CDCl$_3$) δ: 0.88 (t, 3H), 1.2, 1.4 (each m, 20H), 1.49, 1.62 (each m, 2H), 2.45 (t, 2H), 3.83 (s, 3H), 6.72, 6.75 (each m, 2H), 8.88 (broad s, 1H).

SYNTHESIS EXAMPLE 4

Synthesis of 3-tridecylpyrrole

Into a mixture of 9.50 g (30.9 mmol) of methyl 4-tridecylpyrrole-2-carboxylate obtained in Synthesis Example 3,200 ml of ethylene glycol and 10 ml of water, was added 20 g of potassium hydroxide and the mixture was heated at 190° C. under stirring for 5 hours. After cooling, the mixture was added with water and extracted with ethyl acetate. The organic layer was collected, washed with water, dried over anhydrous magnesium sulfate and then evaporated. The residue was purified by a silica-gel column chromatography (eluent: ethyl acetate/hexane=1/5) to obtain 7.50 g of 3-tridecylpyrrole. The yield was 97% and the melting point was 32.5° to 33.5° C.

IR (KBr) cm$^{-1}$: 3420, 2950, 2860, 765.

$^1$HNMR (CDCl$_3$, 250 MHz) δ: 0.88 (3H, t), 1.25 (20H, m), 1.57 (2H, m), 2.48 (2H, t), 6.09 (1H, m), 6.57 (1H, m), 6.72 (1H, m), 7.97 (1H, broad s).

EXAMPLE 1

Synthesis of 4-tridecylpyrrole-2-aldehyde (Compound No. 4 in Table 1)

Into a solution of 2.49 g (10 mmol) of 3-tridecylpyrrole obtained in Synthesis Example 4 and 1.62 g (12 mmol) of N-methylformanilide in 25 ml of ethylene chloride, was added dropwise 1.01 ml (11 mmol) of phosphorus oxychloride under stirring with cooling by ice. After refluxing 30 minutes, the mixture was cooled to room temperature and was added with 10 ml of aqueous solution containing 6.0 g of sodium acetate, followed by refluxing for 15 minutes.

The reaction solution was extracted with ethyl acetate and the organic layer was separated. The organic layer was washed with a diluted hydrochloric acid and then a saturated aqueous solution of sodium chloride, dried over anhydrous magnesium sulfate, and then evaporated. The residue was purified by a silicagel column chromatography (eluent: ethyl acetate/hexane=1/10) to obtain 0.32 g of 4-tridecylpyrrole-2-aldehyde. The yield was 12% and the melting point was 61° to 64° C.

IR (KBr) cm$^{-1}$: 3220, 2940, 2860, 1690, 1645, 1400, 1390, 765.

NMR (CDCl$_3$) δ: 0.88 (3H, t), 1.26 (20H, m), 1.54 (2H, m), 2.47 (2H, t), 6.80 (1H, m), 6.90 (1H, m), 9.20 (1H, broad s), 9.44 (1H, s).

SYNTHESIS EXAMPLE 5

Synthesis of methyl 4-dodecanoylpyrrole-2-carboxylate

In the same manner as in Synthesis Example 1 using 213 g (1.06 mol) of lauric acid as the starting substance, was obtained 245.5 g of methyl 4-dodecanoylpyrrole-2-carboxylate. The yield was 90% and the melting point was 102° to 103° C.

IR (KBr) cm$^{-1}$: 3270, 2920, 2850, 1690, 1660.

NMR (CDCl$_3$) δ: 0.88 (3H, t), 1.25 (16H, m), 1.70 (2H, m), 2.75 (2H, t), 3.88 (3H, s), 7.30 (1H, m), 7.53 (1H, m), 9.50 (1H, broad s).

SYNTHESIS EXAMPLE 6

Synthesis of methyl 4-(1-hydroxydodecyl)pyrrole-2-carboxylate

A mixture of 245.5 g (0.80 mol) of methyl 4-dodecanoylpyrrole-2-carboxylate obtained in Synthesis Example 5, 1.5 liter of tetrahydrofuran and 0.15 liter of methanol was added with 15.1 g (0.40 mol) of sodium borohydride little by little at a temperature of 10° to 21° C. under stirring. The mixture was stirred at 20° C. for one hour and 7.5 g (0.20 mol) of sodium borohydride was further added thereto. After one-hour stirring at 20° C., the solvent was evaporated and 700 ml of water and 2.4 liter of ethyl acetate were added to the residue. The organic layer was collected, washed with 700 ml of water and then 700 ml of a saturated aqueous solution of sodium chloride, dried over anhydrous magnesium sulfate, and then evaporated to obtain 247.0 g of pale brownish crystals. The yield was 99%.

IR (KBr) cm$^{-1}$: 3450, 3240, 2930, 1680.

NMR (CDCl$_3$) δ: 0.88 (3H, t), 1.25 (18H, m), 1.73 (2H, m), 3.85 (3H, s), 4.63 (1H, m), 6.88 (1H, m), 6.92 (1H, m), 9.05 (1H, broad s).

SYNTHESIS EXAMPLE 7

Synthesis of methyl 4-(1-acetoxydodecyl)pyrrole-2-carboxylate

Into a solution of 247.0 g (0.80 mol) of methyl 4-(1-hydroxydodecyl)pyrrole-2-carboxylate obtained in Synthesis Example 6 in 1.6 liter of toluene, were added 180 ml (1.91 mol) of acetic anhydride and 180 ml (2.23 mol) of pyridine, and the mixture was heated at 105° C. for 2.5 hours. After cooling to room temperature, the mixture was washed twice with 700 ml of 2N hydrochloric acid and was added with 1.2 liter of a saturated aqueous solution of sodium hydrogencarbonate, followed by stirring at room temperature for 30 minutes. The organic layer was collected, washed with 700 ml of a saturated aqueous solution of sodium hydrogencarbonate and then 700 ml of a saturated aqueous solution of sodium chloride, and dried over anhydrous magnesium sulfate. The crystals obtained by removing the solvent by evaporation was recrystallized from 700 ml of hexane to obtain 258.0 g of pale brownish crystals. The yield was 92% and the melting point was 69° to 70° C.

IR (KBr) cm$^{-1}$: 3300, 2920, 1705.

NMR (CDCl$_3$) δ: 0.88 (3H, t), 1.25 (18H, m), 1.86 (2H, m), 2.03 (3H, s), 3.85 (3H, s), 5.73 (1H, t), 6.89 (1H, m), 6.95 (1H, m), 9.08 (1H, broad s).

SYNTHESIS EXAMPLE 8

Synthesis of methyl 4-dodecylpyrrole-2-carboxylate

Into a solution of 258.0 g (0.73 mol) of methyl 4-(1-acetoxydodecyl)pyrrole-2-carboxylate obtained in Synthesis Example 7 in 2.0 liter of ethanol, was added 16 g of 10% palladium-carbon and a catalytic hydrogenation was carried out at 50° C. under a hydrogen atmosphere. The catalytic hydrogenation was completed after 5.5 hours. Then, 1.5 liter of chloroform was added and the catalyst was filtered off. The solvent was removed from the filtrate by evaporation to obtain crystals. The crystals were recrystallized from 950 ml of ethanol to obtain 179.6 g of methyl 4-dodecylpyrrole-2-carboxylate as white crystals. The yield was 83% and the melting point was 68° to 69° C.

IR (KBr) cm$^{-1}$: 3340, 2920, 1690.

NMR (CDCl$_3$) δ: 0.88 (3H, t), 1.25 (18H, m), 1.54 (2H, m), 2.44 (2H, t), 3.83 (3H, s), 6.74 (2H, m), 8.88 (1H, broad s).

SYNTHESIS EXAMPLE 9

Synthesis of 4-dodecylpyrrole-2-carboxylic acid hydrazide

In 75 ml of ethanol, 3.57 g (12 mmol) of methyl 4-dodecylpyrrole-2-carboxylate obtained in Synthesis Example 8 was reacted with 15 ml of hydrazine hydrate (100%) under reflux for 36 hours. After cooling, the precipitated crystals were collected by filtration to obtain 3.30 g of 4-dodecylpyrrole-2-carboxylic acid hydrazide as white crystals. The yield was 92% and the melting point was 137° to 139.5° C.

IR (KBr) cm$^{-1}$: 3320, 2940, 2860, 16458 1540.

NMR (DMSO-d$_6$) δ: 0.84 (3H, t), 1.22 (18H, m), 1.45 (2H, m), 2.33 (2H, t), 4.25 (2H, broad s), 6.55 (1H, m), 6.59 (1H, m), 8.60 (1H, s), 9.11 (1H, s).

SYNTHESIS EXAMPLE 10

Synthesis of 4-dodecylpyrrole-2-carboxylic acid p-toluenesulfonylhydrazide

Into a mixture of 3.29 g (11 mmol) of 4-dodecylpyrrole-2-carboxylic acid hydrazide obtained in Synthesis Example 9 and 35 ml of pyridine, was added little by little 2.23 g (12 mmol) of p-toluenesulfonyl chloride under stirring and cooling with ice. The reaction was carried out for 1.5 hours at room temperature, and the reaction mixture was added to an iced water containing 70 ml of 6N hydrochloric acid. The crystals precipitated by stirring were collected by filtration, washed with water and recrystallized from a mixed solvent of ethanol/water (10/1) to obtain 4.55 g of 4-dodecylpyrrole-2-carboxylic acid p-toluenesulfonylhydrazide as white crystals. The yield was 91% and the melting point was 134.5° to 135.5° C.

IR (KBr) cm$^{-1}$: 3420, 3330, 2940, 2860, 1650, 1540, 1335, 1165.

NMR (CDCl$_3$) δ: 0.88 (3H, t), 1.26 (18H, m), 1.53 (2H, m), 2.38 (3H, s), 2.43 (2H, t), 6.54 (1H, m), 6.71 (1H, m), 7.23 (2H, d), 7.38 (1H, d), 7.78 (2H, d), 7.86 (1H, d), 8.95 (1H, broad s).

EXAMPLE 2

Synthesis of 4-dodecylpyrrole-2-aldehyde (Compound No. 3 in Table 1)

An ethylene glycol solution of 2.27 g (5.1 mmol) of 4-dodecylpyrrole-2-carboxylic acid p-toluenesulfonylhydrazide obtained in Synthesis Example 10 was heated to 160° C. and 1.35 g (13 mmol) of sodium carbonate was added thereto at once, followed by further heating for 1.5 minutes. After cooling to room temperature, the reaction mixture was added with water and extracted with ethyl acetate. The organic layer was collected, washed with water, dried over anhydrous magnesium sulfate and evaporated to obtain a crude product. The same procedure as above was repeated in the same scale. The combined crude product was purified by a silica-gel column chromatography (eluent:ethyl acetate/hexane=1/10) to obtain crystals. The crystals were recrystallized from a mixed solvent of ethanol/water to obtain 1.12 g of 4-dodecylpyrrole-2-aldehyde as pale yellow crystals. The yield was 42% and the melting point was 64° to 65° C.

IR (KBr) cm$^{-1}$: 3200, 2940, 2860, 1690, 1650, 1405, 775.

NMR (CDCl$_3$) δ: 0.88 (3H, t), 1.26 (18H, m), 1.57 (2H, m), 2.48 (2H, t), 6.80 (1H, m), 6.91 (1H, m), 9.38 (1H, broad s), 9.44 (1H, s).

EXAMPLE 3

Synthesis of 4-tetradecylpyrrole-2-aldehyde
(Compound No. 5 in Table 1)

In accordance with the procedure in Example 2, 4-tetradecylpyrrole-2-aldehyde was obtained in the yield of 43%. The melting point was 70° to 71° C.

IR (KBr) cm$^{-1}$: 3320, 2940, 2860, 1685, 1650, 1400, 770.

NMR (CDCl$_3$) δ: 0.88 (3H, t), 1.26 (22H, m), 1.57 (2H, m), 2.48 (2H, t), 6.80 (1H, m), 6.91 (1H, m), 9.40 (1H, broad s), 9.44 (1H, s).

SYNTHESIS EXAMPLE 11

Synthesis of methyl
4-methoxyvinylpyrrole-2-carboxylate

Into a solution of 200 g (0.58 mol) of methoxymethyltriphenylphosphonium chloride in 1.5 liter of tetrahydrofuran, was added dropwise 220 ml of a tetrahydrofuran solution (2.01 mol concentration) containing 0.44 mol of lithium diisopropylamide under stirring and cooling with ice. After one-hour stirring at room temperature, 400 ml of a tetrahydrofuran solution of 57.6 g (0.38 mol) of methyl 4-formylpyrrole-2-carboxylate was added to the mixture at 5° to 8° C. under cooling with ice. The reaction was carried out for one hour at room temperature, and the reaction mixture was added with water and extracted with ethyl acetate. The organic layer was collected, washed with a saturated solution of sodium chloride, dried over anhydrous magnesium sulfate and evaporated to obtain a residue. The residue was purified by a silica-gel column chromatography (eluent:ethyl acetate/hexane=¼) to obtain 34.4 g of methyl 4-methoxyvinylpyrrole-2-carboxylate as a mixture of E-isomer and Z-isomer. The yield was 50%.

NMR (CDCl$_3$) δ: 3.63 (s, E-isomer), 3.76 (s, Z-isomer), 3.85 (3H, s), 5.20 (d, Z-isomer, J=6.5 Hz), 5.68 (d, E-isomer, J=13 Hz), 6.01 (d, Z-isomer), 6.82 (2H, m), 7.00 (1H, m), 7.17 (1H, m), 9.10 (1H, broad s).

SYNTHESIS EXAMPLE 12

Synthesis of
(2-methoxycarbonylpyrrole)-4-acetaldehyde

Into a solution of 13.0 g (72 mmol) of methyl 4-methoxyvinylpyrrole-2-carboxylate obtained in Synthesis Example 11, 280 ml of isopropyl alcohol and 280 ml of water, was added 1.13 g of p-toluenesulfonic acid and the mixture was refluxed for 3.5 hours. After cooling, the reaction mixture was added with a saturated solution of sodium chloride and extracted with ethyl acetate. The organic layer was collected, washed with an aqueous solution of sodium chloride containing small amount of sodium hydrogencarbonate, and dried over anhydrous magnesium sulfate. The residue obtained by evaporation was purified by a silica-gel column chromatography (eluent:ethyl acetate/hexane=2/5) to obtain 7.50 g of oily (2-methoxycarbonyl-pyrrole)-4-acetaldehyde. The yield was 62%.

IR (Neat) cm$^{-1}$: 3340, 1720, 1695, 1220, 770.

NMR (CDCl$_3$) δ: 3.57 (2H, t), 3.85 (3H, s), 6.81 (1H, m), 6.88 (1H, m), 9.26 (1H, broad s), 9.72 (1H, d).

SYNTHESIS EXAMPLE 13

Synthesis of methyl
4-(2-tridecenyl)pyrrole-2-carboxylate

A mixture of 14.1 g (60 mmol) of undecyl bromide and 15.7 g (60 mmol) of triphenylphosphine was refluxed in xylene for 15 hours, and the xylene was evaporated off. The mixture was added with ether and the supernatant was removed by decantation. This procedure was repeated thrice to obtain 19.3 g of undecyltriphenylphosphonium bromide. The bromide was dissolved in 200 ml of tetrahydrofuran and 20 ml (32 mmol) of a hexane solution (1.6 molar concentration) of 15% n-butyl lithium was added dropwise thereto under stirring and cooling with ice. After 10-minute stirring, a solution of 2.17 g (13 mmol) of (2-methoxycarbonylpyrrole)-4-acetaldehyde obtained in Synthesis Example 12 in 6 ml of tetrahydrofuran was added dropwise to the mixture under cooling with ice, and the mixture was allowed to react for 30 minutes. The reaction mixture was added with water and extracted with ethyl acetate. The organic layer was collected, washed with a saturated aqueous solution of sodium chloride and dried over anhydrous magnesium sulfate. The residue obtained by evaporation was purified by a silica-gel column chromatography (eluent:ethyl acetate/hexane=1/10) to obtain 3.41 g of oil methyl 4-(2-tridecenyl)pyrrole-2-carboxylate. The yield was 86%.

IR (Neat) cm$^{-1}$: 3340, 2940, 2860, 1690, 770,

NMR (CDCl$_3$) δ: 0.88 (3H, t), 1.26 (16H, m), 2.00, 2.20 (each 2H, m), 3.17, 3.22 (each 2H, d), 3.83 (3H, s), 5.50 (2H, m), 6.74 (2H, m), 8.95 (1H, broad s).

SYNTHESIS EXAMPLE 14

Synthesis of 4-(2-tridecenyl)pyrrole-2-carboxylic acid hydrazide

By using 3.69 g (12 mmol) of methyl 4-(2-tridecenyl)-pyrrole-2-carboxylate obtained in Synthesis Example 13 and in accordance with the procedure in Synthesis Example 9, 3.39 g of 4-(2-tridecenyl)pyrrole-2-carboxylic acid hydrazide was obtained in white crystals. The yield was 92% and the melting point was 129.5° to 131.5° C.

IR (KBr) cm$^{-1}$: 3310, 2930, 2860, 1640, 1620, 1530,

NMR (CDCl$_3$) δ: 0.88 (3H, t), 1.26 (16H, m), 2.08 (2H, m), 3.15, 3.22 (each 2H, d), 4.02 (2H, s), 5.49 (2H, m), 6.43 (1H, m), 6.73 (1H, m), 7.30 (1H, s), 9.40 (1H, broad s).

SYNTHESIS EXAMPLE 15

Synthesis of 4-(2-tridecenyl)pyrrole-2-carboxylic acid p-toluenesulfonylhydrazide By using 3.38 g (11 mmol) of 4-(2-tridecenyl)pyrrole-2-carboxylic acid hydrazide obtained in Synthesis Example 14 and in accordance with the procedure in Synthesis Example 10, 4.81 g of 4-(2-tridecenyl)pyrrole-2-carboxylic acid p-toluenesulfonylhydrazide was obtained in white crystals. The yield was 94% and the melting point was 131.5° to 133° C.

IR (KBr) cm$^{-1}$: 3320, 2930, 2860, 1645, 1540, 1160.

NMR (CDCl$_3$) δ: 0.88 (3H, t), 1.26 (16H, m), 2.10 (2H, m), 3.15, 3.21 (each 2H, d), 5.50 (2H, m), 6.54 (1H, m), 6.72 (1H, m), 7.24 (2H, d), 7.35 (1H, d), 7.78 (2H, d), 7.85 (1H, d), 8.96 (1H, broad s).

EXAMPLE 4

Synthesis of 4-(2-tridecenyl)pyrrole-2-aldehyde (Compound No. 33 in Table 1)

By using 4.80 g of 4-(2-tridecenyl)pyrrole-2-carboxylic acid p-toluenesulfonylhydrazide obtained in Synthesis Example 15 and in accordance with the procedure in Example 2, 1.45 g of 4-(2-tridecenyl)pyrrole-2-aldehyde was obtained in pale yellow crystals. The yield was 50% and the melting point was 29° to 32° C.

IR (KBr) cm$^{-1}$: 3300, 2940, 2860, 1650, 1400, 785.

NMR (CDCl$_3$) δ: 0.88 (3H, t), 1.26 (16H, m), 2.00, 2.10 (each 2H, m), 3.19, 3.25 (each 2H, d), 5.50 (2H, m), 6.80 (1H, m), 6.93 (1H, m), 9.44 (1H, s), 9.60 (1H, broad s).

TEST EXAMPLE 1

The effect of reducing lipids by the action of the compounds according to the present invention was measured as follows.

To each group of 6 Wister male rats weighing from 140 to 150 g, a test compound suspended in a 0.05% Tween 80 was orally administered by 5, 10 or 20 mg/kg once per day for 8 days.

Blood was sampled three hours after the final administration of the test compound and the amount of triglyceride (TG) in serum was determined by an enzymatic method using a neutral fat measuring kit, New Clintec (TG) manufactured by Diatron Co.

The amount of cholesterol (Chol) was measured by another enzymatic method using a cholesterol determining kit, Determina-TC5 manufactured by Kyowa Medix Co.

The reduction rate (%) were determined for each amount of TG and Chol in comparison with those of control group to which the test compound was not applied. The results are shown in Table 2 below.

TABLE 2

| Compound No. | Dose (mg/kg) | TG Reduction (%) | Chol Reduction (%) |
|---|---|---|---|
| No.3 | 10 | 65 | 27 |
| No.3 | 30 | 60 | 43 |
| No.4 | 5 | 31 | 25 |
| No.4 | 10 | 58 | 38 |
| No.4 | 20 | 75 | 52 |
| No.5 | 10 | 53 | 20 |
| No.5 | 30 | 50 | 28 |
| No.33 | 10 | 43 | 32 |
| No.33 | 30 | 60 | 37 |

What is claimed is:

1. A pyrrolealdehyde derivative represented by the following formula (I):

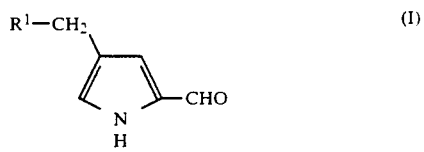

(I)

wherein R$^1$ represents C$_9$–C$_{15}$ alkyl unsubstituted or substituted by at least one substituent selected from the group consisting of halo, hydroxy, amino, carbamoyl, C$_1$–C$_5$ alkylamino, C$_2$–C$_6$ dialkylamino, (C$_1$–C$_5$ alkyl)carbonylamino, C$_1$–C$_5$ alkylthio, mercapto, (C$_1$–C$_5$ alkyl)carbonyloxy, carbamoyloxy, C$_6$–C$_{12}$ aryl and C$_3$–C$_7$ cycloalkyl; or C$_9$–C$_{15}$ alkenyl having at least one vinyl, or a pharmaceutically acceptable salt thereof.

2. A pyrrolealdehyde derivative or a pharmaceutically acceptable salt thereof as defined in claim 1, wherein R$^1$ represents C$_{11}$–C$_{13}$ alkyl unsubstituted or substituted by at least one substituent selected from the group consisting of halo, hydroxy, amino, carbamoyl, C$_1$–C$_5$ alkylamino, C$_2$–C$_6$ dialkylamino, (C$_1$–C$_5$ alkyl)carbonylamino, C$_1$–C$_5$ alkylthio, mercapto, (C$_1$–C$_5$alkyl)carbonyloxy, carbamoyloxy, C$_6$–C$_{12}$ aryl and C$_3$–C$_7$ cycloalkyl; or C$_{11}$–C$_{13}$ alkenyl having at least one vinyl.

3. A pharmaceutical composition for treating hyperlipemia and/or arteriosclerosis comprising a therapeutically effective amount of a pyrrolealdehyde derivative represented by the following formula (I):

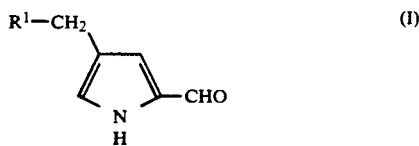

(I)

wherein R$^1$ represents C$_9$–C$_{15}$ alkyl unsubstituted or substituted by at least one substituent selected from the group consisting of halo, hydroxy, amino, carbamoyl, C$_1$–C$_5$ alkylamino, C$_2$–C$_6$ dialkylamino, (C$_1$–C$_5$ alkyl)carbonylamino, C$_1$–C$_5$ alkylthio, mercapto, (C$_1$–C$_5$ alkyl)carbonyloxy, carbamoyloxy, C$_6$–C$_{12}$ aryl and C$_3$–C$_7$ cycloalkyl; or C$_9$–C$_{15}$ alkenyl having at least one vinyl, or a pharmaceutically acceptable salt thereof, in admixture with a pharmaceutically acceptable carrier or diluent.

\* \* \* \* \*